United States Patent
Ibarra

(10) Patent No.: US 10,925,608 B2
(45) Date of Patent: Feb. 23, 2021

(54) DEVICE AND METHOD FOR TREATING NOSEBLEEDS

(71) Applicant: Matthew James Ibarra, Lakewood, CA (US)

(72) Inventor: Matthew James Ibarra, Lakewood, CA (US)

(*) Notice: Subject to any disclaimer, the term of this patent is extended or adjusted under 35 U.S.C. 154(b) by 100 days.

(21) Appl. No.: 16/242,213

(22) Filed: Jan. 8, 2019

(65) Prior Publication Data

US 2019/0133589 A1   May 9, 2019

Related U.S. Application Data

(63) Continuation of application No. 15/146,609, filed on May 4, 2016, now Pat. No. 10,206,684.

(51) Int. Cl.
*A61B 17/12* (2006.01)
*A61B 17/24* (2006.01)
*A61F 13/20* (2006.01)

(52) U.S. Cl.
CPC .............. *A61B 17/12* (2013.01); *A61B 17/24* (2013.01); *A61F 13/2005* (2013.01); *A61B 2017/12004* (2013.01)

(58) Field of Classification Search
CPC .............. A61B 17/12; A61B 17/24; A61B 2017/12004; A61F 13/2005; A61F 13/126; A61F 2013/00476; A61F 5/50; A61F 5/56; A61F 5/566; A61F 5/08; A61F 2005/563

See application file for complete search history.

(56) References Cited

U.S. PATENT DOCUMENTS

| | | | |
|---|---|---|---|
| 4,337,765 A | 7/1982 | Zimmerman | |
| 5,601,093 A | 2/1997 | Sheehan | |
| 10,206,684 B2* | 2/2019 | Ibarra | A61B 17/12 |
| 2004/0194788 A1 | 10/2004 | Sweet | |
| 2006/0237020 A1 | 10/2006 | Morgan et al. | |
| 2008/0193897 A1 | 8/2008 | Kubo et al. | |
| 2009/0165805 A1 | 7/2009 | Syrop et al. | |
| 2012/0085354 A1 | 4/2012 | Polk, III | |
| 2013/0048532 A1 | 2/2013 | Rix | |
| 2013/0298917 A1 | 11/2013 | Poisson et al. | |
| 2014/0261465 A1 | 9/2014 | Turkbas | |
| 2016/0338684 A1* | 11/2016 | Arden | A61B 17/025 |

* cited by examiner

*Primary Examiner* — Jocelin C Tanner
(74) *Attorney, Agent, or Firm* — AKC Patents, LLC; Aliki K. Collins

(57) ABSTRACT

A device for treating nosebleeds includes a mouth insert comprising a horizontally extending elongated portion and a center portion extending downward from a bottom surface of the elongated portion. The center portion comprises a narrower width than the horizontally extending elongated portion and the elongated portion is shaped and dimensioned to be inserted into a buccal cavity of a user's mouth and to fit behind the user's upper lip and in front of the user's upper gums. The center portion is shaped and dimensioned to be positioned only in front of the user's upper front teeth. The center portion comprises a push-structure formed at a bottom end of the center portion and the push-structure comprises a push-surface used for placing a user's tongue or finger and pushing the device upward in order to provide pressure to the user's nose.

19 Claims, 8 Drawing Sheets

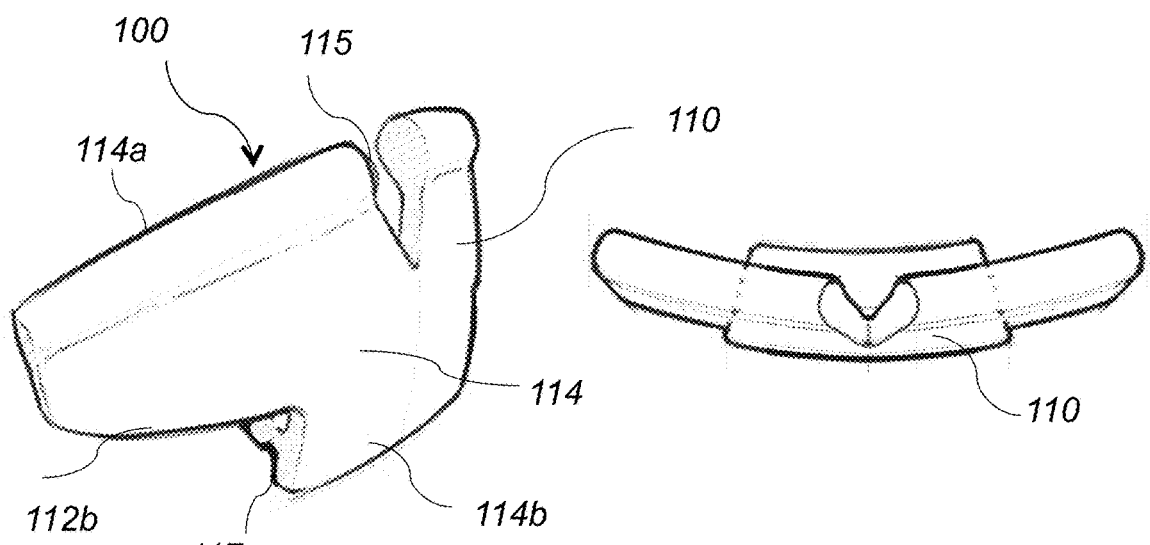
FIG. 3A
FIG. 3B
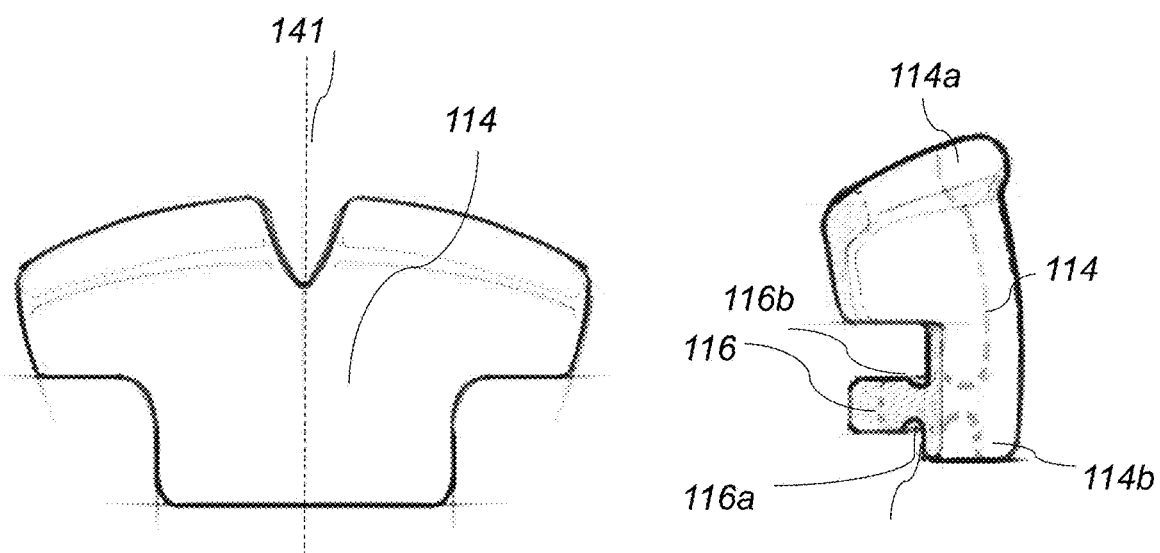
FIG. 3C
FIG. 3D

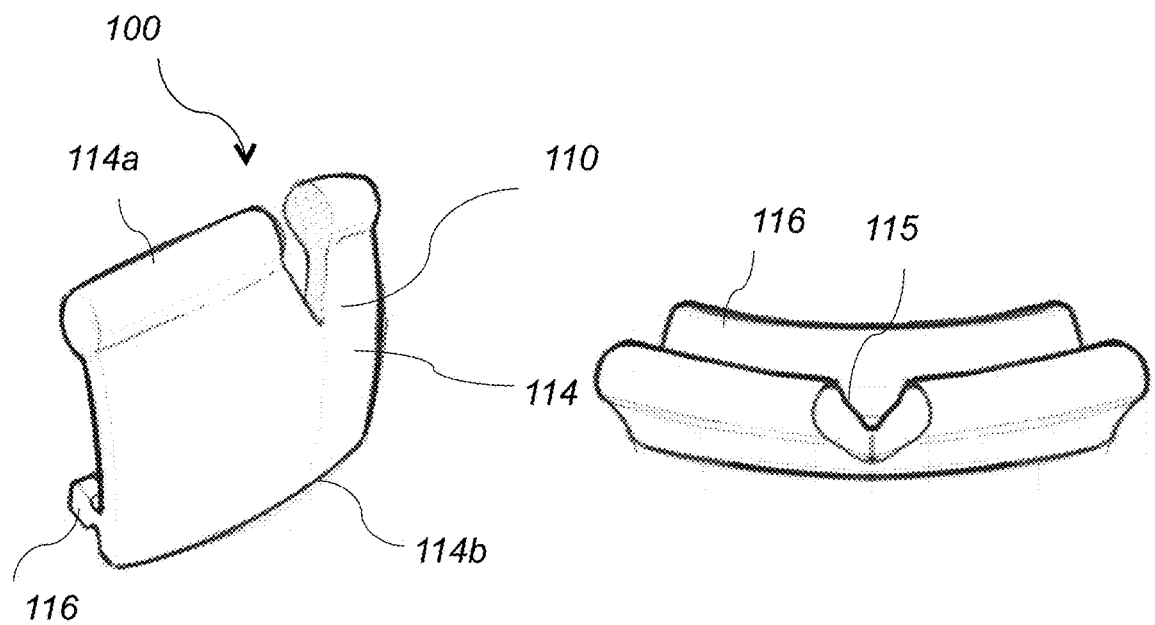
FIG. 4A
FIG. 4B
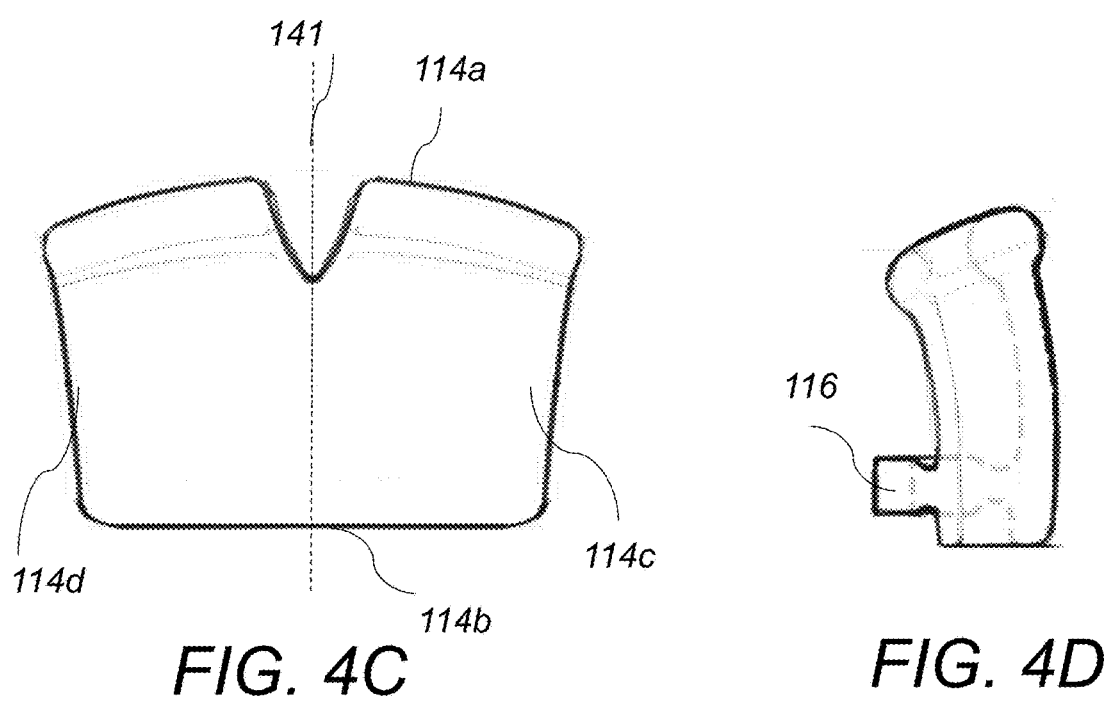
FIG. 4C
FIG. 4D

DEVICE AND METHOD FOR TREATING NOSEBLEEDS

CROSS REFERENCE TO RELATED CO-PENDING APPLICATIONS

This application is a continuation and claims the priority to and benefit of U.S. patent application Ser. No. 15/146,609 filed on May 4, 2016 and entitled DEVICE AND METHOD FOR TREATING NOSEBLEEDS, which is commonly assigned and the contents of which are expressly incorporated herein by reference.

This application also claims the priority to and benefit of U.S. Provisional Patent Application Ser. No. 62/158,197 filed on May 7, 2015 and entitled NOSEBLEED TOURNIQUET DEVICE, which is commonly assigned and the contents of which are expressly incorporated herein by reference.

FIELD OF THE INVENTION

The present invention relates to a device and a method for treating nosebleeds, and more particularly to a device and a method for stopping or slowing nosebleeds in humans by applying pressure under the upper lip of a user.

BACKGROUND OF THE INVENTION

A typical method for treating nosebleeds or epistaxis in a patient includes positioning the patient upright, leaning forward slightly and firmly pinching the outside of the nose with the thumb and index fingers just below the bone against the face. Other methods include applying cold packs, cauterization, nasal packing or even surgery. However, pinching the nose, cauterization, nasal packing and surgery usually cause discomfort and pain to the patient. Therefore, there is a need for a non-invasive, painless and simple technique for stopping nosebleeds.

SUMMARY OF THE INVENTION

In general, in one aspect, the invention features a device for treating nosebleeds including a mouth insert comprising a horizontally extending elongated portion and a center portion extending downward from a bottom surface of the elongated portion. The center portion comprises a narrower width than the horizontally extending elongated portion and the elongated portion is shaped and dimensioned to be inserted into a buccal cavity of a user's mouth and to fit behind the user's upper lip and in front of the user's upper gums. The center portion is shaped and dimensioned to be positioned only in front of the user's upper front teeth. The center portion comprises a push-structure formed at a bottom end of the center portion and the push-structure comprises a push-surface used for placing a user's tongue or finger and pushing the device upward in order to provide pressure to the user's nose.

Implementations of this aspect of the invention may include one or more of the following features. The push-structure is dome-shaped. The push-surface is convex. The push-surface is concave. The elongated portion comprises a circular cross-section. The elongated portion comprises a U-shaped gap dimensioned to fit around the user's frenulum. The elongated portion comprises left and right components arranged to left and right sides of the U-shaped gap, respectively. The left and right components of the elongated portion comprise cylindrical shapes. The left and right components of the elongated portion comprise conical shapes. The left and right components of the elongated portion comprise oval shapes. The left and right components of the elongated portion comprise soft, flexible or porous materials. The elongated portion and the center portion are curved backwards and have a curvature radius that matches the user's upper gum line radius. The elongated portion comprises an adjustable width. The elongated portion comprises cut-away features on left and right sides of the elongated portion and the cut-away features are designed to tear off and thereby to reduce the width of the device. The elongated portion comprises foldable extensions on left and right sides of the elongated portion and wherein the foldable extensions are designed to unfold and thereby to increase the width of the device. The mouth insert is made of semi-rigid materials comprising one of silicone, latex, rigid or flexible polypropylene, cotton gauze, other forms of cotton, or pressed paper mold. A top surface of the elongated portion is covered with an inverted U-shaped component and wherein the U-shaped component comprises one of soft, flexible or porous materials. The center portion comprises one or more openings configured to add flexibility to the device.

In general, in another aspect, the invention features a method for treating nosebleeds including the following. First, providing a mouth insert comprising a horizontally extending elongated portion, a center portion extending downward from a bottom surface of the elongated portion, wherein the center portion comprises a narrower width than the horizontally extending elongated portion, wherein the elongated portion is shaped and dimensioned to be inserted into a buccal cavity of a user's mouth and to fit behind the user's upper lip and in front of the user's upper gums, wherein the center portion is shaped and dimensioned to be positioned only in front of the user's upper front teeth and wherein the center portion comprises a push-structure formed at a bottom end of the center portion and wherein the push-structure comprises a push-surface. Next, inserting the mouth insert into a buccal cavity of a user's mouth and then placing a user's tongue or finger onto the push-surface and applying pressure upward to the user's buccal cavity and towards an anterior portion of the user's nose.

Among the advantages of this invention may be one or more of the following. The invention provides a device and a method for stopping or slowing a nosebleed without medications, invasive operations, contact with the nasal passages or pain to the patient.

The details of one or more embodiments of the invention are set forth in the accompanying drawings and description below. Other features, objects and advantages of the invention will be apparent from the following description of the preferred embodiments, the drawings and from the claims.

BRIEF DESCRIPTION OF THE DRAWINGS

Referring to the figures, wherein like numerals represent like parts throughout the several views:

FIG. 3A is a perspective view of a second embodiment of the device for treating nosebleeds according to this invention;

FIG. 3B is a top view of the device of FIG. 3A;

FIG. 3C is a front view of the device of FIG. 3A;

FIG. 3D is a side view of the device of FIG. 3A;

FIG. 4A is a perspective view of a third embodiment of the device for treating nosebleeds according to this invention;

FIG. 4B is a top view of the device of FIG. 4A;

FIG. 4C is a front view of the device of FIG. 4A;

FIG. 4D is a side view of the device of FIG. 4A;

DETAILED DESCRIPTION OF THE INVENTION

Figure 1A:
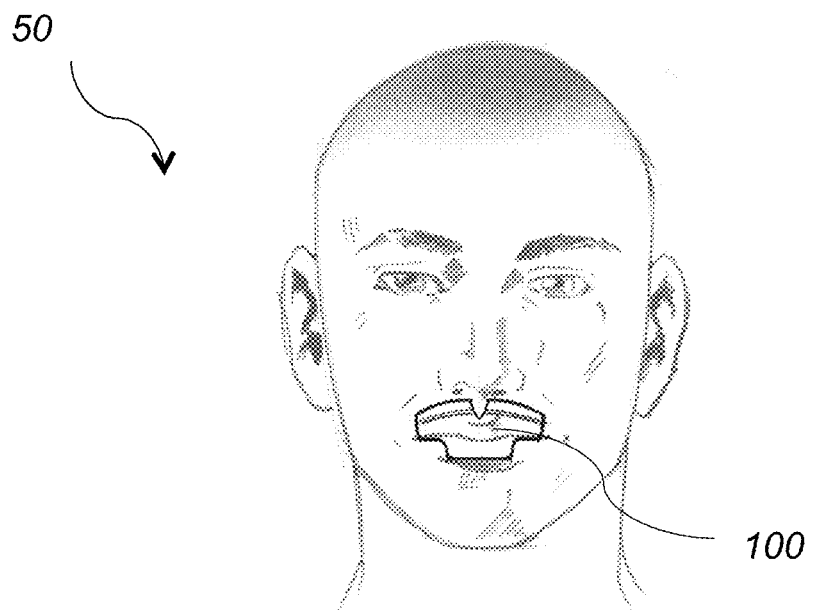
FIG. 1A is a front view of a user with a device according to this invention inserted inside the user's mouth under the upper lip.
Figure 1B:
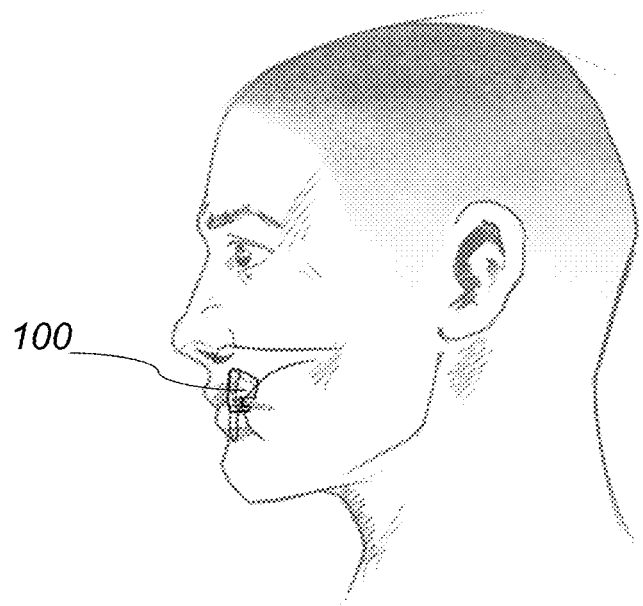
FIG. 1B is a side view of the user of FIG. 1A with the device according to this invention inserted inside the user's mouth under the upper lip.

Referring to FIG. 2A-FIG. 2D, a device 100 for treating nosebleeds includes an elongated body 110, shaped and dimensioned to be inserted into the buccal cavity of a user's 50 mouth and to fit behind the user's upper lip and in front of the user's upper gums, as shown in FIG. 1A. The top portion of device 110 includes a gap 115 extending along the midline 141. Gap 115 has a V-shape and is dimensioned to fit around the user's frenulum, without interfering with the frenulum, which is located at the sagittal plane and top of the gum line. Elongated body 110 includes a central portion 114 having a top 114a, a bottom 114b and left and right portions 112a, 112b that extend sidewise from the central portion 114. Top 114a, has a cylindrical cross section and together with the central portion 114 curves backwards and has a curvature radius that matches the radius of the user's upper gum line. Bottom 114b extends backwards and forms a "bite" tab 116. The central portion 114 is shaped and dimensioned to be positioned in front of the user's upper front teeth and the bite tab 116 is shaped and dimensioned to provide a biting surface for the user's upper front teeth. In this case, the central portion 114 and the bite tab 116 form a structure that has the shape of a J-hook and wraps around the user's front top teeth, as shown in FIG. 1B. Left and right portions 112a, 112b are shaped and dimensioned to fit the user's left and right sides of the upper gums, respectively.

In operation, the user 50 inserts the device 100 in the mouth and places the elongated body 110 behind the upper lip and in front of the top gums, while the bite tab 116 wraps around the top teeth. Next, the user bites down on the bite tab 116 and the biting action causes the top 114a and the central portion 114 to apply pressure upward towards the anterior portion of the nose. The applied pressure blocks the blood flow to the nose and the anterior arteries and causes device 100 to act as a tourniquet that reduces and stops nosebleeds.

As was mentioned above, the elongated body 110 is shaped and dimensioned to be inserted into the buccal cavity of a user's 50 mouth and to fit behind the user's upper lip and in front of the user's upper gums, as shown in FIG. 1A. In one example, device 100 is dimensioned to fit an adult user's mouth and has a width W in the range of 2-3 inches and a height H in the range of ¾ to 1¼ inches. The thickness of the material T is in the range of ⅛ to ¼ inches. Gap 115 has a width w1 in the range of ¼ to ½ inches and a height h1 of about ½ inch. Bite tab 116 extends from front to back by a distance D that is in the range of ½ to 1 inch. Children sizes of the tourniquet device 100 typically range 50-70% of the above mentioned approximate sizes.

A package of several tourniquet devices is provided that includes several comfortable size options for men, women, and children. Alternatively, a single large device 100 is provided that has adjustable width W to fit users with various mouth sizes. In this case, device 100 includes cut-away features or extensions 118 on the left and right portions 112a, 112b, as shown in FIG. 2C. Cut away features 118 are designed to tear off and thereby to shrink the width of the device so that it fits a user with a smaller mouth. Extensions 118 are unfolded to enlarge the width of the device to accommodate a user with a larger mouth.

Device 100 is made of semi-rigid materials including silicone, latex, rigid and flexible polypropylene, cotton gauze, other forms of cotton, or pressed paper molds, among others. Elongated body 110 may be provided in a straightened form and may be bendable to conform to the user's mouth curvature. Alternatively, elongated body 110 may be provided in an already backwards-curved form. The entire device 100 may be flexible or rigid. In cases where device 100 is rigid it may still retain some flexibility to be able to conform to the user's mouth anatomy. The outer surfaces of the elongated body 110 are usually smooth and the edges and corners are rounded in order to provide a comfortable feel while being in contact with the user's gums and tissue and to prevent discomfort, pain or damage of the user's gums.

Referring to FIG. 3A-FIG. 3D, in another embodiment, device 100 for treating nosebleeds includes an elongated body 110, shaped and dimensioned to be inserted into the buccal cavity of a user's 50 mouth and to fit behind the user's upper lip and in front of the user's upper gums, as shown in FIG. 1A. The top portion of device 110 includes a gap 115 in the midline. Gap 115 is shaped and dimensioned to fit around the user's frenulum, so that it does not interfere with the frenulum, which is located at the sagittal plane and top of the gum line. Elongated body 110 includes a central portion 114 having a top 114a, a bottom 114b and left and right portions 112a, 112b that extend sidewise. Top 114a, has a cylindrical cross section and together with the central portion 114 curves backwards and has a curvature radius that matches the radius of the user's upper gum line. Bottom 114b extends downwards from the central portion 114 and has a backwards extending "bite" tab 116. The central portion 114 is shaped and dimensioned to be positioned in front of the user's upper front teeth and the bite tab 116 is shaped and dimensioned to provide a biting surface for the user's front teeth. Bite tab 116 is formed at a distance 117 above the bottom end 114b and includes a semi-circled notch 116a at the bottom surface of tab 116 that extends from the left to the right sides of the central portion 114. Notch 116a provides a bite surface for the bottom teeth of the user to register on the device 100. Bite tab 116 also includes a semi-circled notch 116b at the top surface of tab 116 that is shaped to accommodate the user's top teeth.

Referring to FIG. 4A-FIG. 4D, in another embodiment, a device 100 for treating nosebleeds includes an elongated body 110, shaped and dimensioned to be inserted into the buccal cavity of a user's 50 mouth and to fit behind the user's upper lip and in front of the user's upper gums, as shown in FIG. 1A. The top portion of device 110 includes a gap 115 in the midline. Gap 115 is shaped and dimensioned to fit around the user's frenulum, so that it does not interfere with the frenulum, which is located at the sagittal plane and top of the gum line. Elongated body 110 includes a central portion 114 having a top 114a, a bottom 114b and left and right sides 114c, 114d. Top 114a, has a cylindrical cross section and together with the central portion 114 curves backwards and has a curvature radius that matches the radius of the user's upper gum line. Bottom 114b has a backwards extending "bite" tab 116. The central portion 114 is shaped and dimensioned to be positioned in front of the user's upper front teeth and the bite tab 116 is shaped and dimensioned to provide a biting surface for the user's front teeth. Bite tab 116 is formed at a distance 117 above the bottom end 114b and includes a semi-circled notch 116a at the bottom surface of tab 116 that extends from the left to the right sides of the central portion 114. Notch 116a provides a bite surface for the bottom teeth of the user to register on the device 100. Bite tab 116 also includes a semi-circled notch 116b at the top surface of tab 116 that is shaped to accommodate the user's top teeth. In this case, central portion 114 extends the entire width W of the elongated body 110. Bite tab 116 also extends the entire width of central portion 114 and the elongated body 110 from the left side 114c to the right side 114d and provides a wider bite surface than in the cases of FIG. 2A and FIG. 3A.

Figure 2A:
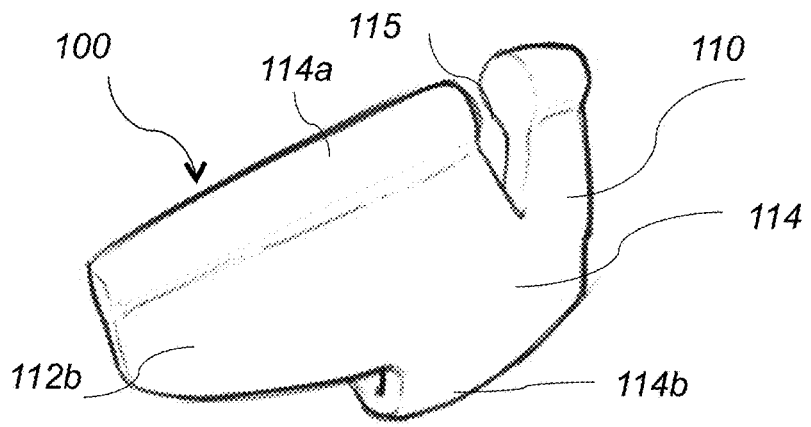
FIG. 2A is a perspective view of a first embodiment of the device for treating nosebleeds according to this invention.
Figure 2B:
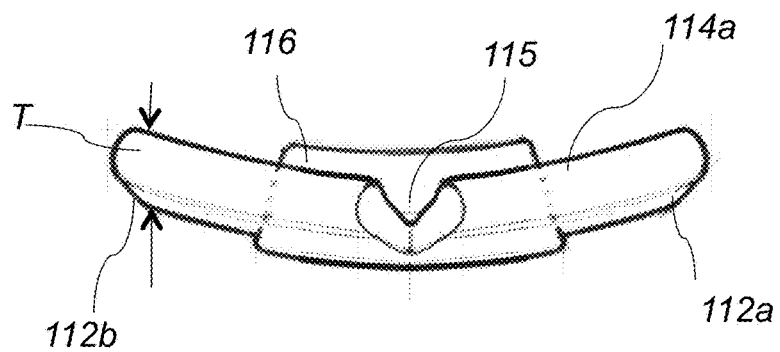
FIG. 2B is a top view of the device of FIG. 2A.
Figure 2C:
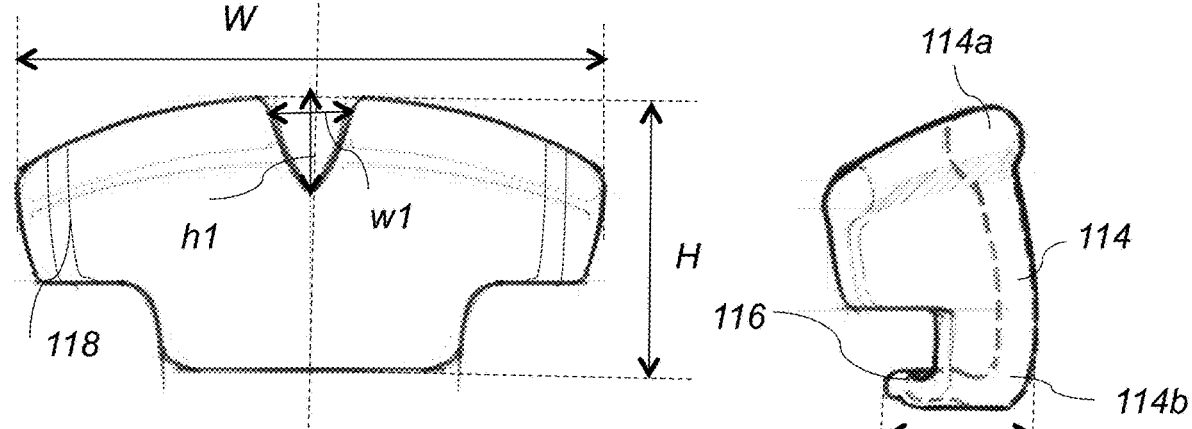
FIG. 2C is a front view of the device of FIG. 2A.
Figure 2D:
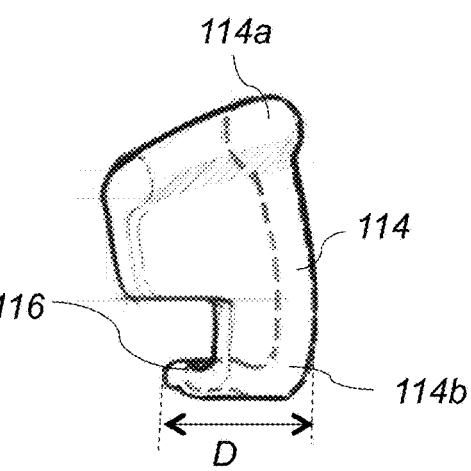
FIG. 2D is a side view of the device of FIG. 2A.
Figure 5:
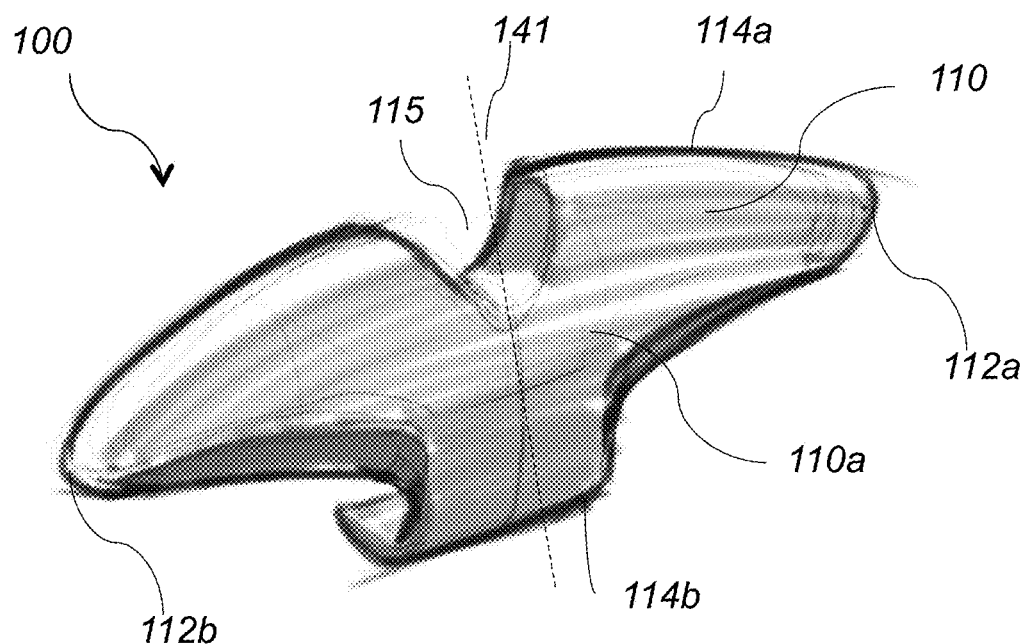
FIG. 5 is a perspective view of a fourth embodiment of the device for treating nosebleeds according to this invention.

Referring to FIG. 5, device 100 has the same geometry and features as device 100 of FIG. 2A. In this case, the front surface 110a is straight from left to right and the thickness of body 110 varies from the top 114a to bottom 114b and at various cross sections from left portion 112a to right portion 112b. Device 100 is made of semi-rigid material and can conform to the anatomy of the user's mouth when placed inside the upper-lip.

Figure 6:
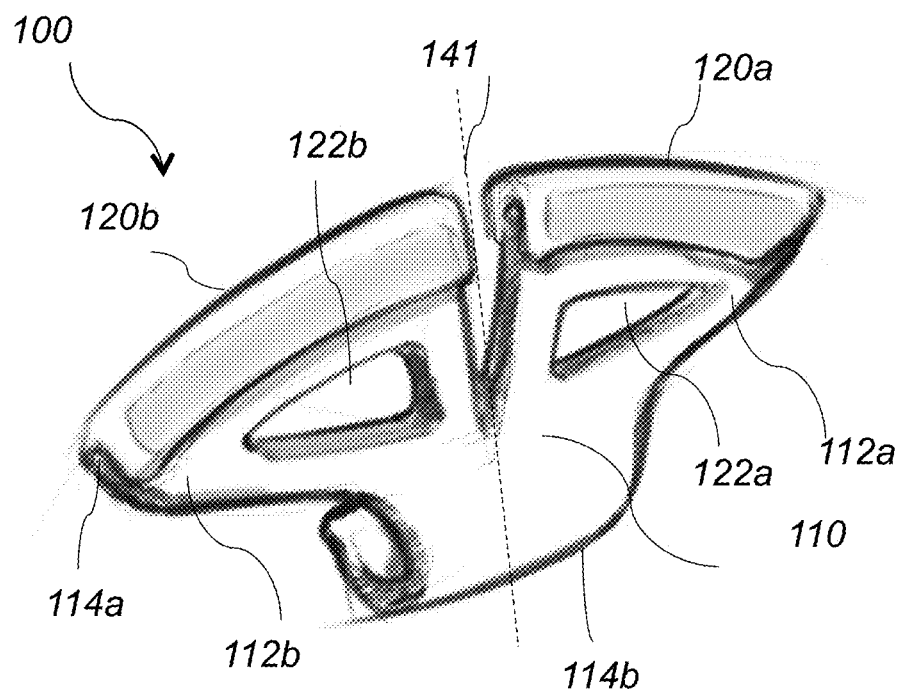
FIG. 6 is a perspective view of a fifth embodiment of the device for treating nosebleeds according to this invention.

Referring to FIG. 6, device 100 has the same geometry and features as device 100 of FIG. 2A. In this case, a first "U" shaped component 120a covers the left top surface 114a of the main body 110 and a second "U" shaped component 120b covers the right top surface 114a of the main body 110. The U-shaped components 120a, 120b are made of a soft, or flexible, or porous material. Examples of preferred materials for the U-shaped components 120a, 120b include silicone, latex, rigid and flexible polypropylene, cotton gauze, or some form of cotton or pressed paper molds. The U-shaped components 120a, 120b are designed to provide comfort during usage. There are also two openings 122a and 122b at the left and right portions 112a, 112b of the main body 110, respectively. These openings 122a, 122b are designed to provide added flexibility, especially if the material is more rigid.

Figure 7:
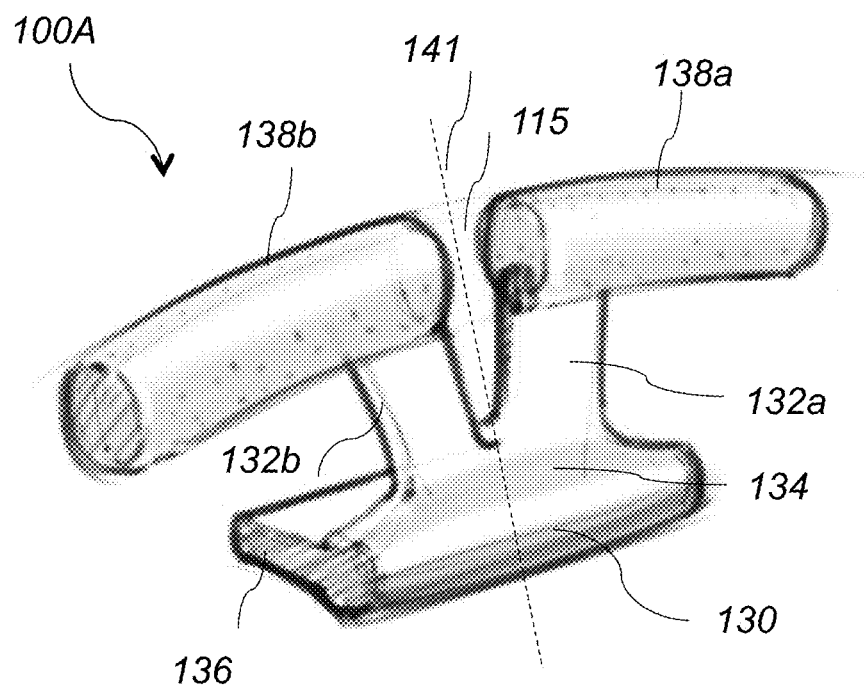
FIG. 7 is a perspective view of a sixth embodiment of the device for treating nosebleeds according to this invention.

Referring to FIG. 7, device 100A for treating nosebleeds includes a semi-rigid body 130 having a backwards extending bite tab 136, left and right portions 132a, 132b extending upwards from the top surface 134 of the body 130 and forming a V-shaped structure with a central gap 115. Device 100A also includes left and right cylindrical structures 138a, 138b extending horizontally and being attached to the top ends of the left and right portions 132a, 132b, respectively. Device 100A is shaped and dimensioned to be inserted into the buccal cavity of a user's 50 mouth and the cylindrical structures 138a, 138b are sized to conform and fit behind the user's upper lip and in front of the user's upper gums, as shown in FIG. 1A. The body 130 is shaped and dimensioned to be positioned in front of the user's upper front teeth and the bite tab 136 is shaped and dimensioned to provide a biting surface for the user's upper front teeth. Left and right cylindrical structures 138a, 138b extend horizontally from the inner sides of the top ends of the left and right portions 132a, 132b, respectively, and end beyond the left and right ends of the bite tab 136. Left and right cylindrical structures 138a, 138b curve downward from the midline to the left and right sides of the device, respectively. Left and right cylindrical structures 138a, 138b are made of a soft, flexible, or porous material. Examples of preferred materials for the left and right cylindrical structures 138a, 138b include silicone, latex, rigid and flexible polypropylene, cotton gauze, or some form of cotton or pressed paper molds. Gap 115 is shaped and dimensioned to fit around the user's frenulum, so that it does not interfere with the frenulum, which is located at the sagittal plane and top of the gum line.

Figure 8:
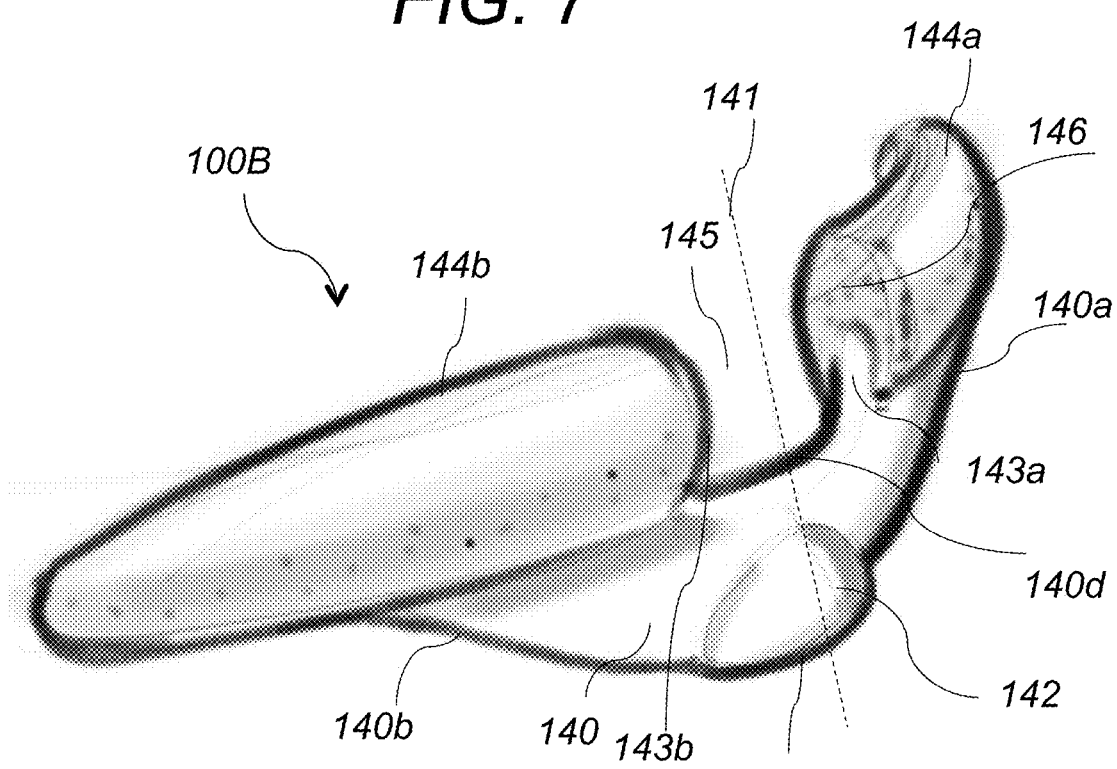
FIG. 8 is a perspective view of a seventh embodiment of the device for treating nosebleeds according to this invention.
Figure 9:
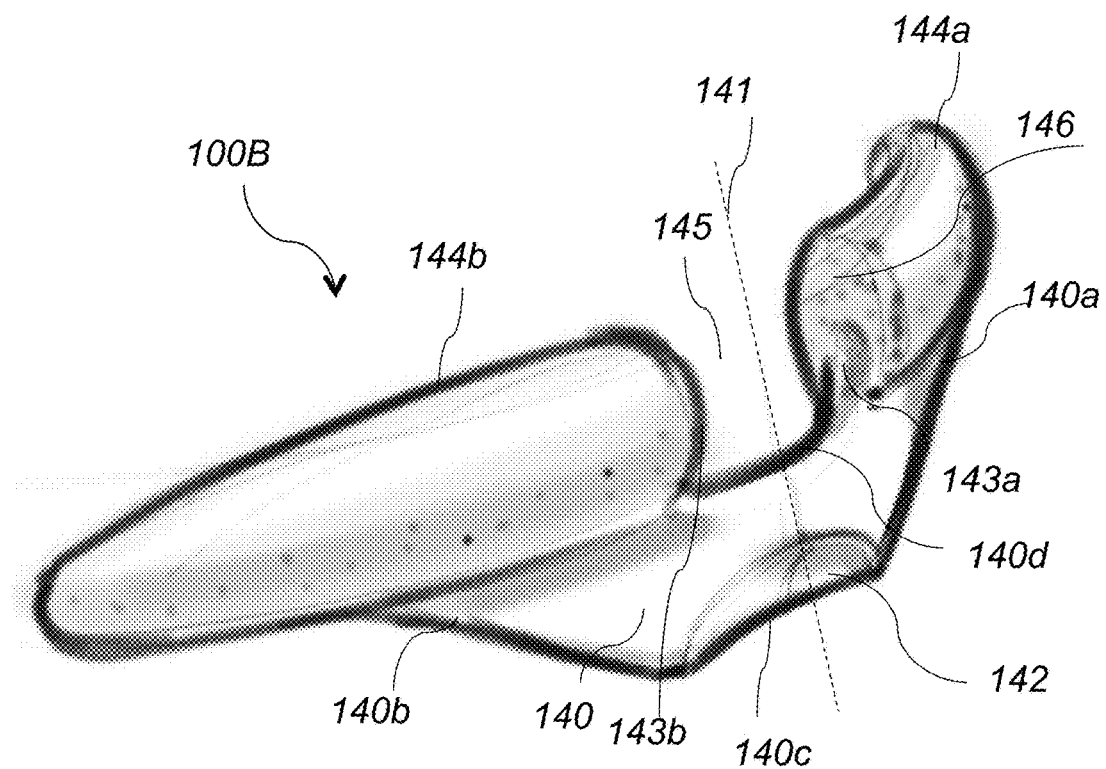
FIG. 9 is a perspective view of an eighth embodiment of the device for treating nosebleeds according to this invention.

Referring to FIG. 8 and FIG. 9, device 100B for treating nosebleeds includes a semi-rigid elongated body 140 that symmetrically curves inward from the midline 141 to the left and right sides 140a, 140b of the device. Elongated body 140 has a dome-shaped structure 142 formed at the middle bottom end 140c of body 140. Dome-shaped structure 142 is convex in FIG. 8 and concave in FIG. 9. Dome-shaped structure 142 provides a push surface for placing a user's tongue or finger and pushing the device upward in order to provide pressure to the nose. The top end 140d of body 140 includes a U-shaped cut 145 and left and right top ends 143a, 143b. U-shaped cut 145 is shaped and dimensioned to fit around the user's frenulum, so that it does not interfere the frenulum. Left and right top ends 143a, 143b are covered with left and right conical structures 144a, 144b, respectively. Left and right conical structures 144a, 144b have oval shaped cross-sections 146 and extend from the inner sides of the top ends 143a, 143b respectively, and end beyond the left and right sides 140a, 140b of the elongated body 140, respectively. Conical structures 144a, 144b are sized to conform and fit behind the user's upper lip and in front of the user's upper gums. Semi-rigid elongated body 140 is made of silicone, latex, rigid and flexible polypropylene, cotton gauze, or some form of cotton or pressed paper molds. Left and right structures 144a, 144b are made of soft, flexible or porous material including silicone, latex, porous gauze, porous cotton, or porous pressed paper molds, among others.

Figure 10:
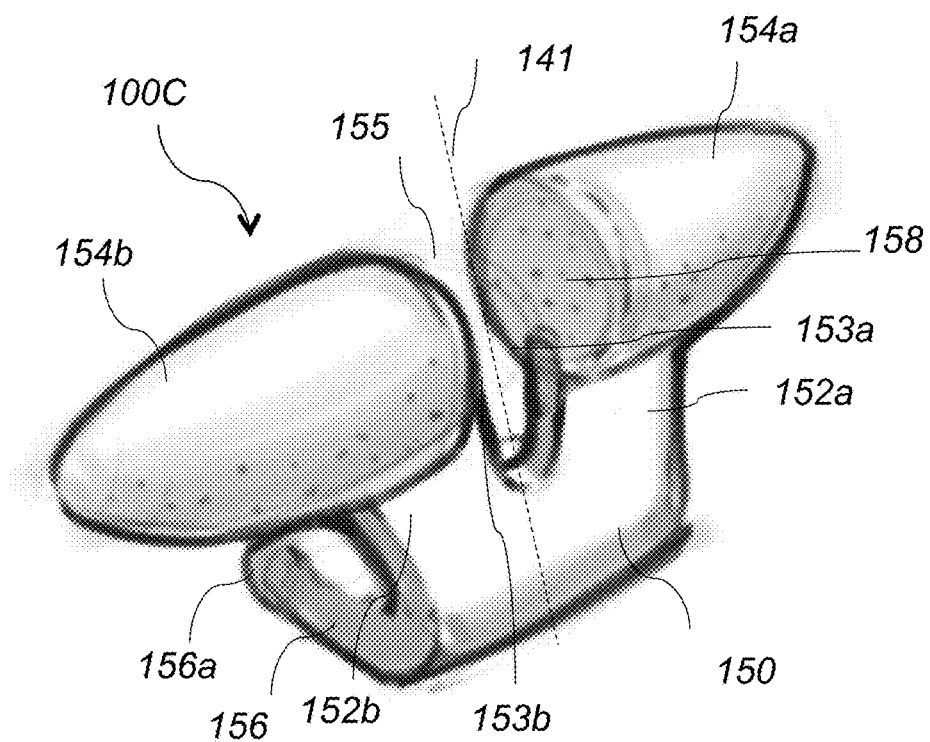
FIG. 10 is a perspective view of a ninth embodiment of the device for treating nosebleeds according to this invention.

Referring to FIG. 10, device 100C for treating nosebleeds includes a semi-rigid body 150 having a backwards extending bite tab 156, left and right portions 152a, 152b extending upwards from the top surface of the body 150 and forming a V-shaped structure with a central gap 155. Bite tab 156 extends backwards straight and terminates in a rounded end portion 156a. Device 100C also includes left and right conical structures 154a, 154b extending horizontally and being attached to the top ends of the left and right portions 153a, 153b, respectively. Device 100A is shaped and dimensioned to be inserted into the buccal cavity of a user's 50 mouth and the conical structures 154a, 154b are sized to conform and fit behind the user's upper lip and in front of the user's upper gums, as shown in FIG. 1A. The body 150 is shaped and dimensioned to be positioned in front of the user's upper front teeth and the bite tab 156 is shaped and dimensioned to provide a biting surface for the user's front teeth. Left and right conical structures 154*a*, 154*b* extend horizontally from the inner sides of the top ends of the left and right portions 153*a*, 153*b*, respectively, and end beyond the left and right ends of the bite tab 156. Left and right conical structures 154*a*, 154*b* have circular cross-sections 158. Semi-rigid body 150 is made of silicone, latex, rigid and flexible polypropylene, cotton gauze, or some form of cotton or pressed paper molds. Left and right structures 154*a*, 154*b* are made of soft, flexible or porous material including silicone, latex, porous gauze, porous cotton, or porous pressed paper molds, among others. Gap 155 is shaped and dimensioned to fit around the user's frenulum, so that it does not interfere with the frenulum, which is located at the sagittal plane and top of the gum line.

Figure 11:
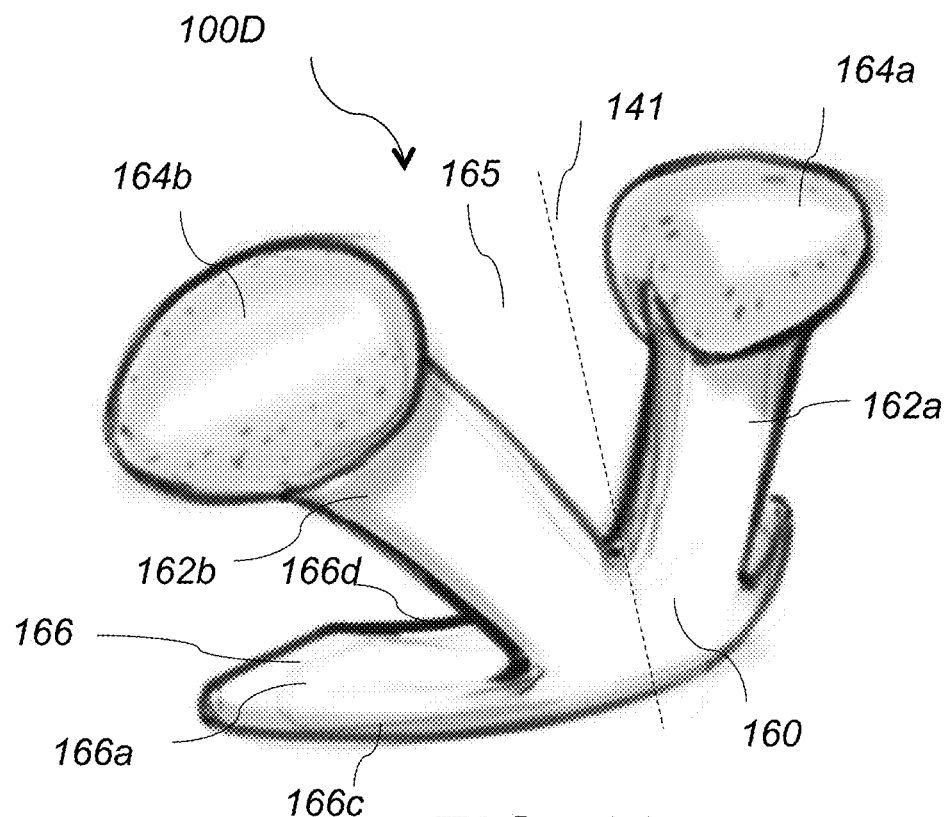
FIG. 11 is a perspective view of a tenth embodiment of the device for treating nosebleeds according to this invention.

Referring to FIG. 11, device 100D for treating nosebleeds includes a semi-rigid body 160 having a backwards extending bite tab 166, left and right portions 162*a*, 162*b* extending upwards from the top surface of the body 160 and forming a V-shaped structure with a central gap 165. Bite tab 166 has a flat top surface 166*a* and curved front 166*c* and back 166*d* edges. Edges 166*c*, 166*d* are curved to follow the alignment of the top teeth. Device 100D also includes left and right oval structures 164*a*, 164*b* extending horizontally and being attached to the top ends of the left and right portions 162*a*, 162*b*, respectively. Device 100D is shaped and dimensioned to be inserted into the buccal cavity of a user's 50 mouth and the oval structures 164*a*, 164*b* are sized to conform and fit behind the user's upper lip and in front of the user's upper gums, as shown in FIG. 1A. The body 160 is shaped and dimensioned to be positioned in front of the user's upper front teeth and the bite tab 166 is shaped and dimensioned to provide a biting surface for the user's front teeth. Left and right oval structures 164*a*, 164*b* extend horizontally from the inner sides of the top ends of the left and right portions 162*a*, 162*b*, respectively, and end beyond the left and right ends of the bite tab 166. Left and right oval structures 164*a*, 164*b* have circular cross-sections. Semi-rigid body 160 is made of silicone, latex, rigid and flexible polypropylene, cotton gauze, or some form of cotton or pressed paper molds. Left and right oval structures 164*a*, 164*b* are made of soft, flexible or porous material including silicone, latex, porous gauze, porous cotton, or porous pressed paper molds, among others. Gap 165 is shaped and dimensioned to fit around the user's frenulum, so that it does not interfere with the frenulum, which is located at the sagittal plane and top of the gum line.

Figure 12:
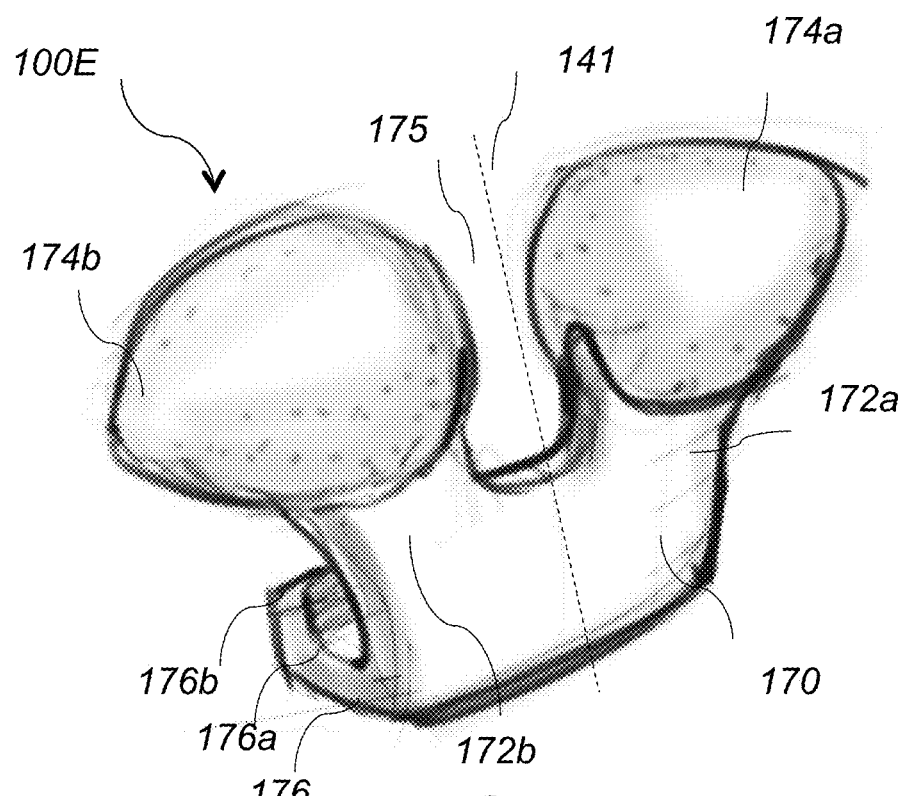
FIG. 12 is a perspective view of an eleventh embodiment of the device for treating nosebleeds according to this invention.

Referring to FIG. 12, device 100E for treating nosebleeds includes a semi-rigid body 170 having a backwards extending bite tab 176, left and right portions 172*a*, 172*b* extending upwards from the top surface of the body 170 and forming a U-shaped structure with a central gap 175. Bite tab 176 has a flat top surface 176*a* and the back edge 176*b* is curved upwards by 90 degrees relative to the top surface 176*a*, forming a J-hook that is configured to wrap around the user's top front teeth. Edge 176*b* extends upwards above the top surface 176*a* by a height in the range of ⅛ to ¼ inch. Device 100E also includes left and right oval structures 174*a*, 174*b* extending horizontally and being attached to the top ends of the left and right portions 172*a*, 172*b*, respectively. Device 100E is shaped and dimensioned to be inserted into the buccal cavity of a user's 50 mouth and the oval structures 174*a*, 174*b* are sized to conform and fit behind the user's upper lip and in front of the user's upper gums, as shown in FIG. 1A. The body 170 is shaped and dimensioned to be positioned in front of the user's upper front teeth and the bite tab 176 is shaped and dimensioned to provide a biting surface for the user's upper front teeth. Left and right oval structures 174*a*, 174*b* extend horizontally from the inner sides of the top ends of the left and right portions 172*a*, 172*b*, respectively, and end beyond the left and right ends of the bite tab 176. Left and right oval structures 174*a*, 174*b* have circular cross-sections. Semi-rigid elongated body 170 is made of silicone, latex, rigid and flexible polypropylene, cotton gauze, or some form of cotton or pressed paper molds. Left and right oval structures 174*a*, 174*b* are made of soft, flexible or porous material including silicone, latex, porous gauze, porous cotton, or porous pressed paper molds, among others. Gap 175 is shaped and dimensioned to fit around the user's frenulum, so that it does not interfere with the frenulum, which is located at the sagittal plane and top of the gum line.

Several embodiments of the present invention have been described. Nevertheless, it will be understood that various modifications may be made without departing from the spirit and scope of the invention. Accordingly, other embodiments are within the scope of the following claims.

What is claimed is:

1. A device for treating nosebleeds comprising:
 a mouth insert comprising a horizontally extending elongated portion, a center portion extending downward from a bottom surface of the elongated portion, wherein the center portion comprises a narrower width than the horizontally extending elongated portion;
 wherein the elongated portion is shaped and dimensioned to be inserted into a buccal cavity of a user's mouth and to fit behind the user's upper lip and in front of the user's upper gums;
 wherein the center portion is shaped and dimensioned to be positioned only in front of the user's upper front teeth; and
 wherein the center portion comprises a push-structure formed at a bottom end of the center portion and wherein the push-structure comprises a push-surface used for placing a user's tongue or finger and pushing the device upward in order to provide pressure to the user's nose.

2. The device of claim 1, wherein the push-structure is dome-shaped.

3. The device of claim 1, wherein the push-surface is convex.

4. The device of claim 1, wherein the push-surface is concave.

5. The device of claim 1, wherein the elongated portion comprises a circular cross-section.

6. The device of claim 1, wherein the elongated portion comprises a U-shaped gap dimensioned to fit around the user's frenulum.

7. The device of claim 6, wherein the elongated portion comprises left and right components arranged to left and right sides of the U-shaped gap, respectively.

8. The device of claim 7, wherein the left and right components of the elongated portion comprise cylindrical shapes.

9. The device of claim 7, wherein the left and right components of the elongated portion comprise conical shapes.

10. The device of claim 7, wherein the left and right components of the elongated portion comprise oval shapes.

11. The device of claim 7, wherein the left and right components of the elongated portion comprise soft, flexible or porous materials.

12. The device of claim 1, wherein the elongated portion and the center portion are curved backwards and have a curvature radius that matches the user's upper gum line radius.

13. The device of claim 1, wherein the elongated portion comprises an adjustable width.

14. The device of claim 13, wherein the elongated portion comprises cut-away features on left and right sides of the elongated portion and wherein the cut-away features are designed to tear off and thereby to reduce the width of the device.

15. The device of claim 13, wherein the elongated portion comprises foldable extensions on left and right sides of the elongated portion and wherein the foldable extensions are designed to unfold and thereby to increase the width of the device.

16. The device of claim 1, wherein the mouth insert is made of semi-rigid materials comprising one of silicone, latex, rigid or flexible polypropylene, cotton gauze, other forms of cotton, or pressed paper mold.

17. The device of claim 1, wherein a top surface of the elongated portion is covered with an inverted U-shaped component and wherein the U-shaped component comprises one of soft, flexible or porous materials.

18. The device of claim 1, wherein the center portion comprises one or more openings configured to add flexibility to the device.

19. A method for treating nosebleeds comprising:
providing a mouth insert comprising a horizontally extending elongated portion, a center portion extending downward from a bottom surface of the elongated portion, wherein the center portion comprises a narrower width than the horizontally extending elongated portion, wherein the elongated portion is shaped and dimensioned to be inserted into a buccal cavity of a user's mouth and to fit behind the user's upper lip and in front of the user's upper gums, wherein the center portion is shaped and dimensioned to be positioned only in front of the user's upper front teeth and wherein the center portion comprises a push-structure formed at a bottom end of the center portion and wherein the push-structure comprises a push-surface;
inserting the mouth insert into a buccal cavity of a user's mouth;
placing a user's tongue or finger onto the push-surface and applying pressure upward to the user's buccal cavity and towards an anterior portion of the user's nose.

* * * * *